US010398710B2

(12) United States Patent
Choi et al.

(10) Patent No.: US 10,398,710 B2
(45) Date of Patent: Sep. 3, 2019

(54) METHOD FOR SCREENING REGULATOR OF MITOCHONDRIAL FISSION

(71) Applicant: INTELLIGENT SYNTHETIC BIOLOGY CENTER, Daejeon (KR)

(72) Inventors: Chul Hee Choi, Daejeon (KR); Eun Soo Kim, Seoul (KR); Kyung Sun Choi, Daejeon (KR); Seung Wook Ryu, Daejeon (KR); Jin Gang Hou, Daejeon (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 15/575,537

(22) PCT Filed: Jul. 2, 2015

(86) PCT No.: PCT/KR2015/006825
§ 371 (c)(1),
(2) Date: Nov. 20, 2017

(87) PCT Pub. No.: WO2016/190480
PCT Pub. Date: Dec. 1, 2016

(65) Prior Publication Data
US 2018/0125864 A1    May 10, 2018

(30) Foreign Application Priority Data

May 22, 2015    (KR) ........................ 10-2015-0071480

(51) Int. Cl.
*A61K 31/58*       (2006.01)
*C07J 9/00*        (2006.01)
*C07J 17/00*       (2006.01)
*A61P 25/16*       (2006.01)
*C07J 5/00*        (2006.01)
*A61K 31/704*      (2006.01)
*G01N 33/50*       (2006.01)

(52) U.S. Cl.
CPC ............ *A61K 31/58* (2013.01); *A61K 31/704* (2013.01); *A61P 25/16* (2018.01); *C07J 5/0015* (2013.01); *C07J 9/00* (2013.01); *C07J 17/005* (2013.01); *G01N 33/502* (2013.01)

(58) Field of Classification Search
None
See application file for complete search history.

(56) References Cited

U.S. PATENT DOCUMENTS

| 2013/0337453 A1 | 12/2013 | Theoharides et al. |
| 2014/0274904 A1 | 9/2014 | Mochly-Rosen et al. |
| 2015/0168379 A1* | 6/2015 | Luo ................... G01N 33/5061 |
| | | 435/7.21 |

FOREIGN PATENT DOCUMENTS

| JP | 2007228855 A | 9/2007 |
| JP | 2013-142070 A | 7/2013 |
| KR | 10-2002-0042020 A | 1/2004 |
| KR | 10-2013-0064761 A | 6/2013 |
| KR | 10-2014-0000733 A | 2/2014 |

OTHER PUBLICATIONS

Chamberlain, Graham R et al, "Targeted dilivery of doxorubicin to mitochondria", ACS Chemical Biology, vol. 8, No. 7, pp. 1389-1395 (2013).
Park, Bonggoo et al, "Neutral sphingomyelinase 2 modulates cytotoxic effects of protopanaxadiol on different human cancer cells", BMC Complementary and Alternative Medicine, vol. 13, No. 194, pp. 1-11 (2013).
Zhang, Rui et al., "20-O-(β-D-glucopyranosyl)-20(S)-protopanaxadiol induces apoptosis via induction of endoplasmic reticulum stress in human colon cancer cells", Oncology Reports, vol. 29, pp. 1365-1370 (2013).
Zhang, Yun-Long et al, "20 (S)-protopanaxadiol triggers mitochondrial-mediated apoptosis in human lung adenocarcinoma A549 cells via inhibiting the PI3K/Akt signaling pathway", The American Journal of Chinese Medicine, 2013, vol. 41, No. 5, pp. 1137-1152 (2013).
First Office Action, Application No. 2017-558528, Japan Patent Office, dated Sep. 25, 2018.
Sun et al., "Ginsenoside Rg3 improves cardiac mitochrondial population quality: Mimetic exercise training", Biochemical and Biophysical Research Communications, 441 (2013), 169-174.

* cited by examiner

*Primary Examiner* — Susan M Hanley
(74) *Attorney, Agent, or Firm* — Gavrilovich, Dodd & Lindsey LLP

(57) ABSTRACT

The present invention is directed to a method for screening a regulator of mitochondrial fission using a cell treated to a protopanaxadiol (PPD)-type ginsenoside compound, a composition therefor, and a kit comprising the composition. As the use of the method for screening the regulator of mitochondrial fission of the present invention enables effective discovery of a formulation capable of preventing, improving, or treating a mitochondria-related disease, the method will be widely used for the development of a therapeutic agent for the mitochondria-related disease.

2 Claims, 9 Drawing Sheets

Specification includes a Sequence Listing.

METHOD FOR SCREENING REGULATOR OF MITOCHONDRIAL FISSION

CROSS REFERENCE TO RELATED APPLICATIONS

This application is a U.S. National Stage Application filed under 35 U.S.C. § 371 and claims priority to International Application No. PCT/KR2015/006825, filed Jul. 2, 2015, which application claims priority to Korean Application No. 10-2015-0071480, filed May 22, 2015, the disclosures of which are incorporated herein by reference in their entirety.

TECHNICAL FIELD

The present invention relates to a method for screening a regulator of mitochondrial fission, more specifically to a method for screening a regulator of mitochondrial fission using a cell treated with a protopanaxadiol (PPD)-type ginsenoside compound, a composition for screening a regulator of mitochondrial fission comprising the protopanaxadiol (PPD)-type ginsenoside compound, and a kit comprising the composition.

BACKGROUND

A mitochondrion is an organelle found in most eukaryotic cells. One of the major functions thereof is oxidative phosphorylation, through which energy derived from metabolism of a fuel material such as glucose or fatty acid is converted into adenosine triphosphate (ATP). ATP is used in driving various energy-requiring biosynthesis and other metabolic activities.

Structurally, the mitochondrion consists of an outer membrane and an inner membrane, and is a dynamic organelle continuously performing movement, fusion, and fission. The mitochondrion is organized in a tubular network, and mitochondrial morphology and number are precisely regulated by mitochondrial fusion-fission machinery. As proteins involved in mitochondrial fusion, mitofusin 1 (Mfn1), mitofusin 2 (Mfn2), Opa1, etc. are known, and Drp1, Fis1, etc. are known as proteins involved in mitochondrial fission.

Meanwhile, major constituents of the mitochondrion were discovered to play an important role in cell death, and thus, significance of mitochondria in cell death has been acknowledged since the 1990s. When cell death is induced, various proteins that regulate cell death, endoplasmic reticulum (ER), calcium ions present in cytoplasm, and other proteins related thereto move to the mitochondrion, and mitochondrial fission and fragmentation are caused by mitochondria-shaping protein. The fragmented mitochondrion loses membrane potential and its outer membrane becomes damaged, thereby increasing permeability of the outer membrane. Due to the increased permeability of the outer membrane, various proteins (e.g., cytochrome-C, etc.) in the mitochondrion are released to the cytoplasm through the outer membrane, and cause damage to the outer membrane, thereby increasing permeability thereof. As the permeability increases, various proteins (e.g., cytochrome-C, etc.) in the mitochondrion are released to the cytoplasm and at the same time, nuclei of the mitochondria agglutinate and mitochondrial DNA is cleaved. As a result, mitochondrial function is disabled, leading to cell death. Such mitochondrial-mediated apoptosis has been widely observed, and in particular, is known to be implicated in pathogenesis of various degenerative diseases such as Parkinson's disease and hereditary optic neuropathy.

In this regard, research has been actively conducted on development of a formulation which can inhibit the mitochondrial damage for the purpose of preventing or treating a disease caused by the mitochondrial damage. For examples, Korean Laid-open Patent Application Nos. 2002-0042020 and 2014-0000733 disclose a dihydroxybenzaldehyde compound which effectively inhibits mitochondrial damage caused by a hydroxy radical and a pharmaceutical composition containing N-terminal Truncated Ubiquitin C-terminal hydrolase-L1 that has an important role in regulating stress inducing the mitochondrial damage as an active ingredient for the prevention and treatment of Parkinson's disease, respectively. Likewise, formulations regulating the mitochondrial damage have been developed, but the formulation development has been slow as it requires a tremendous investment of both time and money to confirm effects of the formulation on the mitochondrial damage. If a method that would enable effective discovery of various regulators of the mitochondrial damage is developed, it is predicted that a formulation for treating a disease caused by the mitochondrial damage can be more effectively developed.

TECHNICAL PROBLEM

The present inventors have made extensive efforts to effectively discover a formulation capable of regulating mitochondrial damage, thus confirming that an inhibitor for mitochondrial damage can be effectively discovered by using a PPD-type ginsenoside compound capable of promoting mitochondrial fission in an isolated cell, thereby completing the present invention.

TECHNICAL SOLUTION

An object of the present invention is to provide a method for screening a regulator of mitochondrial fission using a cell treated with a PPD-type ginsenoside compound.

Another object of the present invention is to provide a composition for screening a regulator of mitochondrial fission comprising a protopanaxadiol (PPD)-type ginsenoside compound.

Still another object of the present invention is to provide a kit for screening a regulator of mitochondrial fission comprising the composition.

ADVANTAGEOUS EFFECT

As a formulation capable of preventing, improving, or treating a mitochondria-related disease can be effectively discovered by using the method for screening the regulator of mitochondrial fission of the present invention, the method will be widely used for the development of a therapeutic agent for the mitochondria-related disease.

BEST MODE

Figure 1:
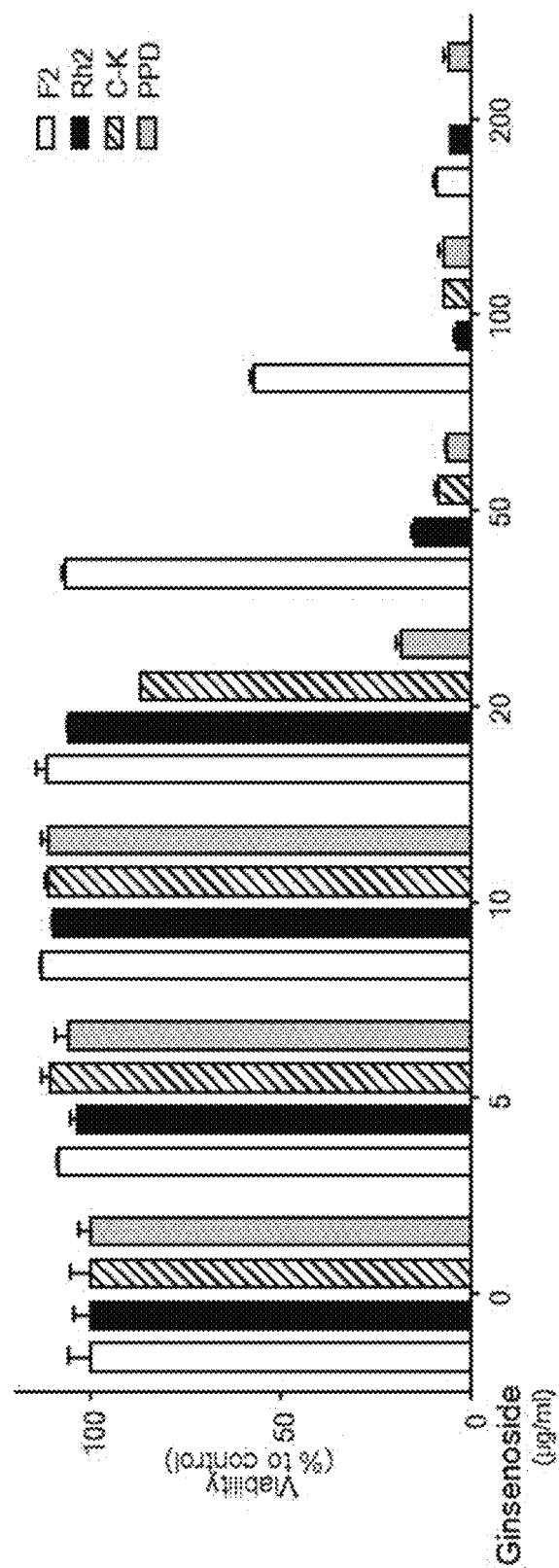
FIG. 1 is a graph showing comparison of effects of the PPD-type ginsenoside compounds (F2, Rh2, C-K, and PPD) at various concentrations (0, 5, 10, 20, 50, 100, and 200 μg/mL) on viability of MCF-7, a breast cancer cell line.

While conducting various studies in order to develop a method to effectively discover a formulation capable of regulating mitochondrial damage, the present inventors focused on mitochondrial fission. Conventionally, mitochondria repeat fission and fusion to regulate their activities. Mitochondria that have undergone fusion perform a major function such as ATP production, while those that have undergone fission improve overall mitochondrial activities by proliferating the number of mitochondria. Additionally, mitochondrial fission occurs in case of fragmentation by mitochondrial damage, and thus is known to play a key role in activating or impairing mitochondria. Accordingly, once a formulation that can regulate the mitochondrial fission is developed, a disease caused by mitochondrial damage can be more effectively treated by using the same.

As described above, mitochondria should be artificially conserved in a fission state in order to develop a formulation regulating mitochondrial fission. While conducting various studies on the development of a formulation capable of inducing mitochondrial fission, the present inventors found that a protopanaxadiol (PPD)-type ginsenoside compound reduces expression of mitochondrial fusion-related proteins (e.g., Mfn2, etc.), while increasing that of mitochondrial fission-related proteins (e.g., OPA-3, etc.).

Accordingly, when a cell treated with the PPD-type ginsenoside compound was treated with a candidate compound expected to regulate mitochondrial fission, thereby verifying whether the cell underwent mitochondrial fission, it was confirmed that a mitochondrial fission regulator could be effectively screened. Such method of regulating mitochondrial fission using the PPD-type ginsenoside compound is not known in the art, and was first developed by the present inventors.

In order to achieve the above-described objects, the present invention provides a method for screening a regulator of mitochondrial fission, comprising treating an isolated cell with a protopanaxadiol (PPD)-treated ginsenoside compound and a candidate compound expected to regulate mitochondrial fission, followed by measuring a level of the mitochondrial fission in the cell.

Specifically, the method for screening a regulator of the mitochondrial fission of the present invention comprises (a) treating an isolated cell with a protopanaxadiol (PPD)-type ginsenoside compound and a candidate compound expected to be capable of regulating mitochondrial fission; (b) measuring a level of mitochondrial fission within the cell treated with the candidate compound; and (c) selecting a candidate compound promoting or inhibiting the mitochondrial fission in comparison with a negative control which is not treated with the candidate compound.

The isolated cell is not limited as long as it can induce mitochondrial fission by the PPD-type ginsenoside compound, and as an example, may be an insulinotropic cell, a cancer cell, etc. The measurement of the mitochondrial fission level can be performed by observing a level of mitochondrial fission using a microscope and measuring expression levels of mitochondrial fusion-related proteins (e.g., Mfn1, Mfn2, OPA1, etc.) or mitochondrial fission-related proteins (e.g., Drp1, Fis1, OPA-3, etc.). For example, when a mitochondrial level increases in a cell treated with the candidate material, the candidate material can be selected as a regulator promoting mitochondrial fission, whereas when a mitochondrial level decreases in a cell treated with the candidate material, the candidate material can be selected as a regulator inhibiting mitochondrial fission. When a mitochondrial fusion-related protein expression level decreases in a cell treated with the candidate material, the candidate material can be selected as a regulator promoting mitochondrial fission, whereas when a mitochondrial fusion-related protein expression level increases in a cell treated with the candidate material, the candidate material can be selected as a regulator inhibiting mitochondrial fission. When a mitochondrial fission-related protein expression increases in a cell treated with the candidate material, the candidate material can be selected as a regulator promoting mitochondrial fission, whereas when a mitochondrial fission-related protein expression decreases in a cell treated with the candidate material, the candidate material can be selected as a regulator inhibiting mitochondrial fission.

It is obvious that all methods for measuring such mitochondrial fission known in the art, in addition to the method described above, can be used, and that one of ordinary skill in the art can selectively use the known methods as necessary.

A regulator of mitochondrial fission discovered using the method for screening the same provided in the present invention can either promote or inhibit the mitochondrial fission level, and thus can be used for improving or treating a disease caused by mitochondrial damage induced by mitochondrial fission. The disease caused by mitochondrial damage is not particularly limited, but may be a metabolic disease (diabetes, etc.), a degenerative brain disease (Parkinson's disease, Alzheimer's disease, etc.), hepatosis, myopathy, an autoimmune disease (rheumarthritis, etc.), etc.

As used herein, "protopanaxadiol (PPD)-type ginsenoside compound" refers to a compound having a chemical structure similar to that of PPD.

It can be understood that the PPD-type ginsenoside compound damages mitochondria within a cell, thereby having a role in supporting an anticancer activity of an anticancer agent that shows a mitochondria-mediated anticancer activity. For example, the PPD-type ginsenoside compound can be PPD of Formula 1 below, C-K of Formula 2 below, etc. An extract from *ginseng*, red *ginseng*, etc., and a chemically synthetic compound can be used as the PPD-type ginsenoside compound.

As used herein, "protopanaxadiol (PPD)" refers to a compound indicated by the chemical formula of $C_{30}H_{52}O_3$ and having a molar mass of about 460 Da and the structure of Formula 1 isolated from *ginseng*.

The PPD promotes mitochondrial fission, and further, can be used for screening a formulation capable of regulating mitochondrial fission. A concentration of the PPD that can be used to promote the mitochondrial fission is not limited as long as it does not show cytotoxicity and promotes mitochondrial fission. As an example, a concentration of 10 μg/mL or below can be treated. As another example, a concentration of 0.1 μg/mL to 10 μg/mL can be treated. As still another example, a concentration of 5 μg/mL to 10 μg/mL can be treated.

[Formula 1]

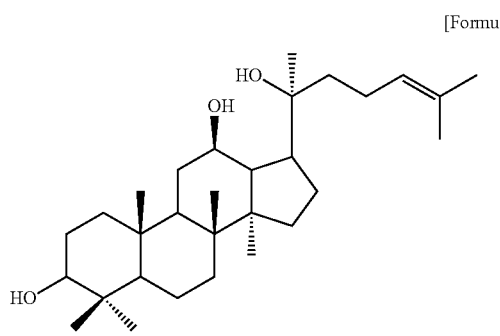

As used herein, "compound-K (C-K)" refers to a ginsenoside compound in a form in which saponin (e.g., ginsenoside Rb1, Rb2, Rc, Rd, etc.) in *ginseng* or red *ginseng* is transformed to be in a form absorbable in vivo by an intestinal microorganism or soil microorganism such as *bifidobacterium*, indicated as a chemical formula of $C_{36}H_{62}O_8$, and having a molar mass of about 622 Da and the structure of Formula 2 below.

The C-K promotes mitochondrial fission, and thus can be used for the method of screening a formulation capable of regulating mitochondrial fission. A concentration which can be used for the mitochondrial fission acceleration is not limited as long as it does not show cytotoxicity and promotes mitochondrial fission. As an example, a concentration of 10 μg/mL or below can be treated. As another example, a concentration of 0.1 μg/mL to 10 μg/mL can be treated. As still another example, a concentration of 5 μg/mL to 10 μg/mL can be treated.

[Formula 2]

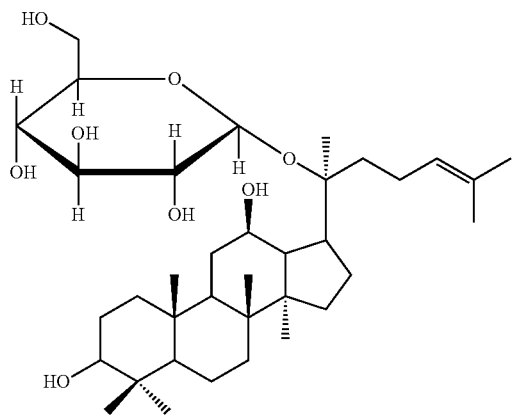

Figure 5A:
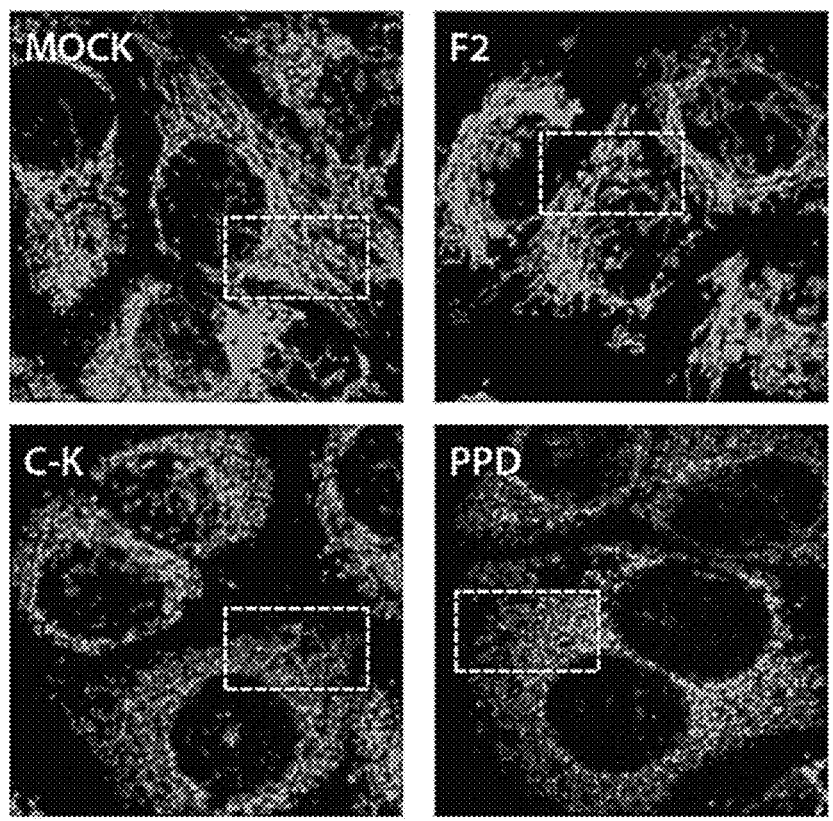
FIG. 5a is an image showing a result of fluorescence staining of mitochondria included in a MCF-7 cell treated with C-K or PPD.
Figure 5B:
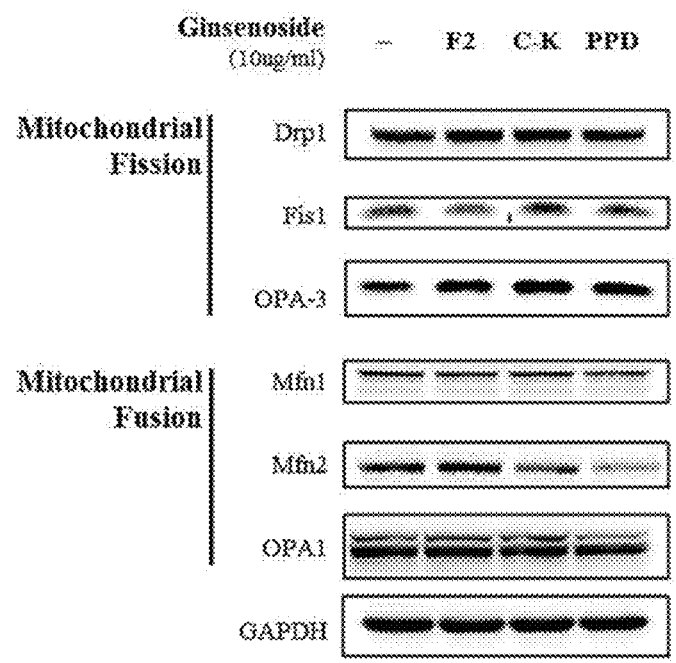
FIG. 5b is an image of Western blot analysis showing expression levels of mitochondrial fission-related proteins (Drp1, Fis1, and OPA-3) and mitochondrial fusion-related proteins (Mfn1, Mfn2, and OPA1), which are expressed in a MCF-7 cell treated with C-K or PPD.

According to an exemplary embodiment of the present invention, the PPD-type ginsenoside compound may exhibit a concentration-dependent anticancer activity against breast cancer cells (FIG. 1); however, it was confirmed that when the compound is treated in an amount that would not show the anticancer activity, part of the compound (C-K or PPD) would inhibit the expression of the mitochondrial fusion-related proteins and promote the expression of the mitochondrial fission-related proteins (FIGS. 5a and 5b).

Accordingly, it can be seen that PPD or C-K, which belongs to the PPD-type ginsenoside compound, promotes mitochondrial fission, and thus can be used for the method of screening a formulation capable of regulating mitochondrial fission.

As another aspect, the present invention provides a composition for screening a regulator of mitochondrial fission comprising the PPD-type ginsenoside compound and kit for screening a regulator of mitochondrial fission, comprising the composition.

The PPD-type ginsenoside compound included in the composition and the kit can promote intracellular mitochondrial fission, and thus can be used for screening a regulator of mitochondrial fission.

In particular, the kit may comprise not only the PPD-type ginsenoside compound, but also one or more kinds of other constitutional compounds, solutions, or devices, which would be appropriate for a method of screening whether a candidate compound can regulate mitochondrial fission. For example, a cell in which mitochondrial fission is promoted by the PPD-type ginsenoside compound, a container used for culturing the cell, a buffer solution appropriate for measuring an expression level of mitochondrial fusion- and fission-related proteins, a fluorescent material (e.g., FITC, RITC, etc.) used for measuring protein expression levels, etc. may be further included.

As a specific example, the kit of the present invention for screening a regulator of mitochondrial fission may be a kit including essential components necessary for performing Western blot analysis that measures an expression level of a mitochondrial fusion- or fission-related protein. In other words, the kit may include a lysis buffer, a first antibody, a second antibody, a formulation for detecting the second antibody, a buffer needed for the Western blot analysis, a test tube, other appropriate containers, etc.

As another example, the kit of the present invention for screening a regulator of mitochondrial fission may be a kit including essential components necessary for measuring an expression level of a mitochondrial fusion- or fission-related protein by performing RT-PCR. In other words, the kit may include a pair of primers specific to the mitochondrial fusion- or fission-related protein, a test tube or other appropriate container, a reaction buffer (various pH values and magnesium concentrations), deoxynucleotides (dNTPs), an enzyme such as Taq-polymerase and reverse transcriptase, a DNase, an RNAse inhibitor, DEPC-water, sterile water, etc. Additionally, the kit may include a pair of primers specific to a gene used as quantitative control.

MODE FOR INVENTION

Hereinafter, the present invention will be described in more detail with reference to Examples. However, these Examples are for illustrative purposes only, and the invention is not intended to be limited by these Examples.

Example 1: Cytotoxicity of Protopanaxadiol (PPD)

Cytotoxicity of the PPD-type ginsenoside compound to a cancer cell was investigated.

First, MCF-7 cells, a human breast cancer cell line, were inoculated in a DMEM culture medium containing 10% FBS and 1% penicillin/streptomycin, and were then cultured at conditions of 37° C. and 5% $CO_2$. When the cultured MCF-7 cells were saturated, subculture thereof was followed in a three- to five-day interval.

The cultured MCF-7 cells were treated with the PPD-type ginsenoside compounds (F2, Rh2, C-K, or PPD) at various concentrations (0, 5, 10, 20, 50, 100, or 200 μg/mL) for 24 hours, and WST-1 analysis was then performed on the cells to measure viability thereof (FIG. 1). The WST-1 analysis was performed by inoculating each cell in a culture medium containing 10% EZ-Cytox and reacting at 37° C. for 1.5 hours, followed by measuring a level of water-soluble formazan dye produced by the viable cells as absorbance (450 nm) and analyzing the same to calculate the cell viability.

FIG. 1 is a graph showing a result of comparison of effects of the PPD-type ginsenoside compounds (F2, Rh2, C-K, and PPD) at various concentrations (0, 5, 10, 20, 50, 100, and 200 μg/mL) on viability of MCF-7, a breast cancer cell line. As shown in FIG. 1, the PPD-type ginsenoside compound was confirmed to show a concentration-dependent anticancer activity against breast cancer cells. The compounds had a little difference from each other, but mostly started showing the anticancer activity when treated at a concentration of 20 μg/mL or above. When treated at a concentration of 200 μg/mL or above, it was confirmed that there was an effect of apoptosis of most of the breast cancer cells. In contrast, it was confirmed that there was no anticancer activity when treated at a concentration of 10 μg/mL or below. In particular, C-K or PPD among the PPD-type ginsenoside compounds was confirmed to show a relatively excellent anticancer activity.

Accordingly, it could be understood that the PPD-type ginsenoside compound shows a concentration-dependent anticancer activity against breast cancer cells.

Example 2: Effect of PPD on Anticancer Effect of Doxorubicin

An effect of the PPD-type ginsenoside compound on the anticancer activity of doxorubicin known as a type of an anticancer agent that shows mitochondria-mediated anticancer activity was studied.

Example 2-1: Effect on Sensitivity to Doxorubicin

In order to investigate an effect of the PPD-type ginsenoside compound on sensitivity of a cancer cell to an anticancer agent, MCF-7, a human breast cancer cell line; C-K or PPD, confirmed to exhibit an excellent anticancer activity in Example 1; tamoxifen, by acting as an antagonist of a hormone receptor, which exhibits an anticancer activity of inhibiting growth of hormone-mediated cancer; and doxorubicin, a type of anticancer agent known to exhibit a mitochondria-mediated anticancer activity, were used.

Specifically, 10 μg/mL of PPD-type ginsenoside compound (F2, Rh2, C-K, or PPD) was added to the MCF-7 cells and was cultured for 12 hours. 20 μM of tamoxifen or 5 μg/mL of doxorubicin was then treated, and 12 hours of culturing was performed. Upon completion of the culturing, viability of MCF-7 cells was compared via WST-1 analysis (FIG. 2a).

Figure 2A:
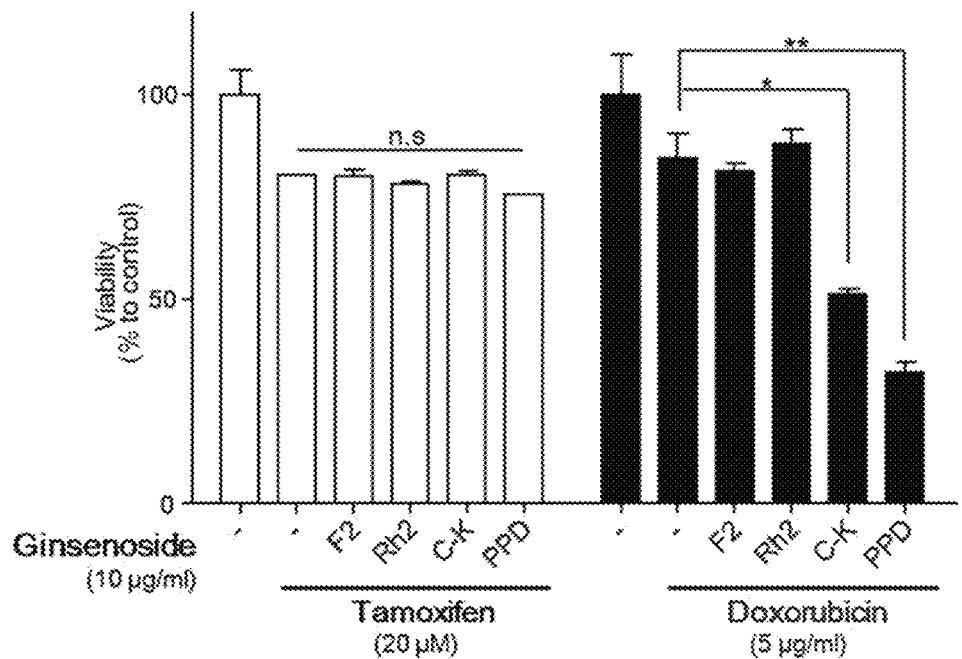
FIG. 2a is a graph showing comparison of effects of the PPD-type ginsenoside compound on anticancer activities of cancer cells.

FIG. 2a is a graph showing comparison of effects of the PPD-type ginsenoside compound on anticancer activities of cancer cells. As shown in FIG. 2a, it was confirmed in Example 1 that as a result of treating the breast cancer cell with the PPD-type ginsenoside compound having a concentration confirmed not to show an anticancer activity at all, followed by treating with an anticancer agent, C-K or PPD among the PPD-type ginsenoside compounds could enhance an anticancer activity by doxorubicin. In contrast, it was confirmed that in the case of treating tamoxifen, any of the PPD-type ginsenoside compound could not enhance the anticancer activity of tamoxifen.

Figure 2B:
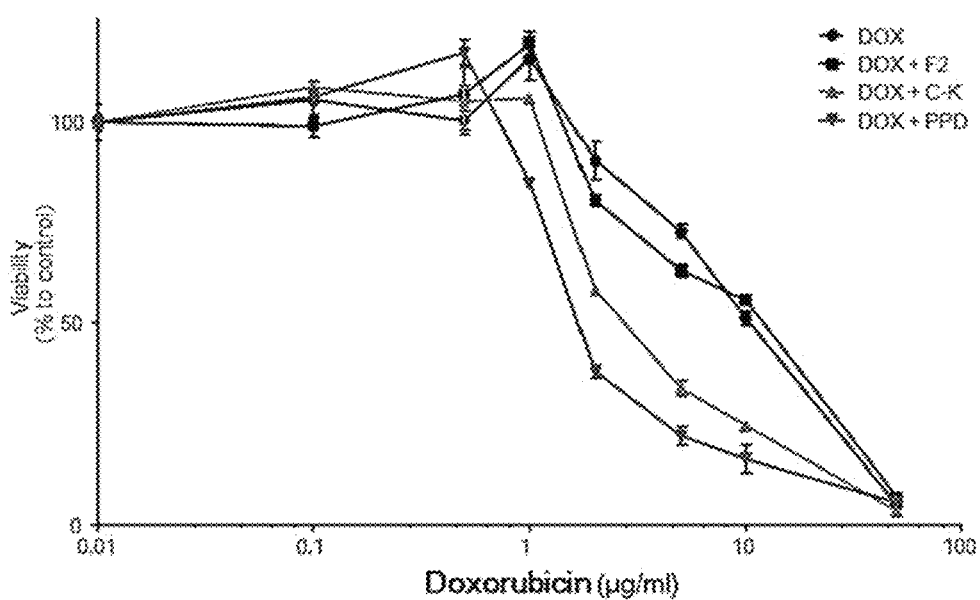
FIG. 2b is a graph showing a result of comparison of viabilities of the breast cancer cells simultaneously treated with C-K or PPD; and doxorubicin at various concentrations. (○), (■), (▲), and (▼) represent the negative control group, the positive control group, the C-K-treated group, and the PPD-treated group, respectively.

Accordingly, in order to investigate whether C-K or PPD has an effect on a treatment concentration of doxorubicin, 10 μg/mL of the PPD-type ginsenoside compound (C-K or PPD) was added and cultured for 12 hours. Doxorubicin at various concentrations (0, 0.1, 0.5, 1, 2, 5, 10, and 50 μg/mL) was then treated and cultured for 24 hours, followed by comparing viabilities of the MCF-7 cells and also comparing LC50 values calculated therefrom via WST-1 analysis (FIG. 2b). An experiment group untreated with ginsenoside and F2, which is a PPD-type ginsenoside compound confirmed not to exhibit a particular effect on doxorubicin, were used as a negative control group and a positive control group, respectively.

FIG. 2b is a graph showing a result of comparison of viabilities of the breast cancer cells simultaneously treated with C-K or PPD; and doxorubicin at various concentrations. (○), (■), (▲), and (▼) represent the negative control group, the positive control group, the C-K-treated group, and the PPD-treated group, respectively. As shown in FIG. 2b, it was confirmed that the anticancer activity increased when C-K or PPD and doxorubicin were treated simultaneously, compared to the case where only doxorubicin was treated. In particular, the LC50 value was about 10 μg/mL when only doxorubicin (negative control) was treated or F2 and doxorubicin were treated at the same time (positive control), whereas the LC50 values were 2 μg/mL and 1.5 μg/mL when C-K and doxorubicin were treated at the same time and PPD and doxorubicin were treated at the same time, respectively. This indicates that C-K or PPD exhibits the effect of enhancing the anticancer activity of doxorubicin.

Example 2-2: Effect on Expression Level of Apoptosis-Related Protein

Figure 3A:
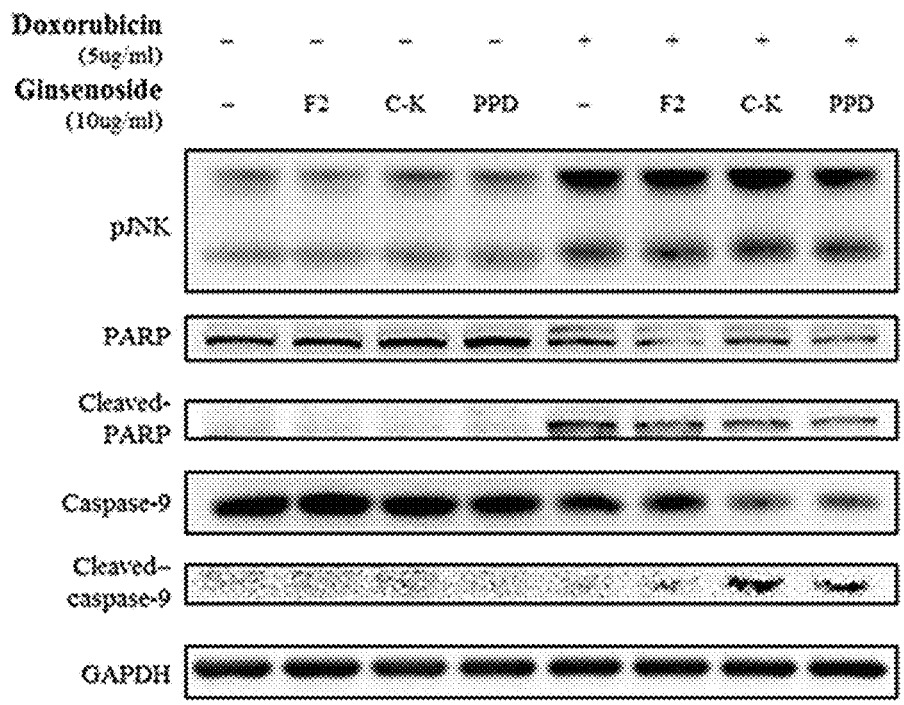
FIG. 3a is an image of Western blot analysis of comparison of expression levels of apoptosis-related proteins in a breast cancer cell simultaneously treated with doxorubicin and C-K or PPD depending on treatment time.

A culture medium containing 10 µg/mL of C-K or PPD was added to the MCF-7 cells, was cultured for 12 hours, and was then replaced with a culture medium containing 10 µg/mL of C-K or PPD and 0 g/mL or 5 µg/mL of doxorubicin, followed by 24 hours of culturing. The cultured cells were destroyed, and Western blot analysis was performed using a pJNK antibody, PARP antibody, cleaved-PARP antibody, caspase-9 antibody, or cleaved-caspase-9 antibody (FIG. 3a). An experiment group untreated with ginsenoside and F2, which is a PPD-type ginsenoside compound confirmed not to exhibit a particular effect on doxorubicin, were used as a negative control group and a positive control group, respectively.

FIG. 3a is an image of Western blot analysis of comparison of expression levels of apoptosis-related proteins in a breast cancer cell simultaneously treated with doxorubicin and C-K or PPD depending on treatment time. As shown in FIG. 3a, levels of pJNK, cleaved-PARP, and cleaved-caspase-9 were increased in all cells treated with doxorubicin. Additionally, the levels of pJNK and cleaved-PARP were not affected by C-K or PPD treatment, whereas the level of cleaved-caspase-9 was noticeably increased by C-K or PPD treatment, and was significantly increased particularly by the PPD treatment.

Figure 3B:
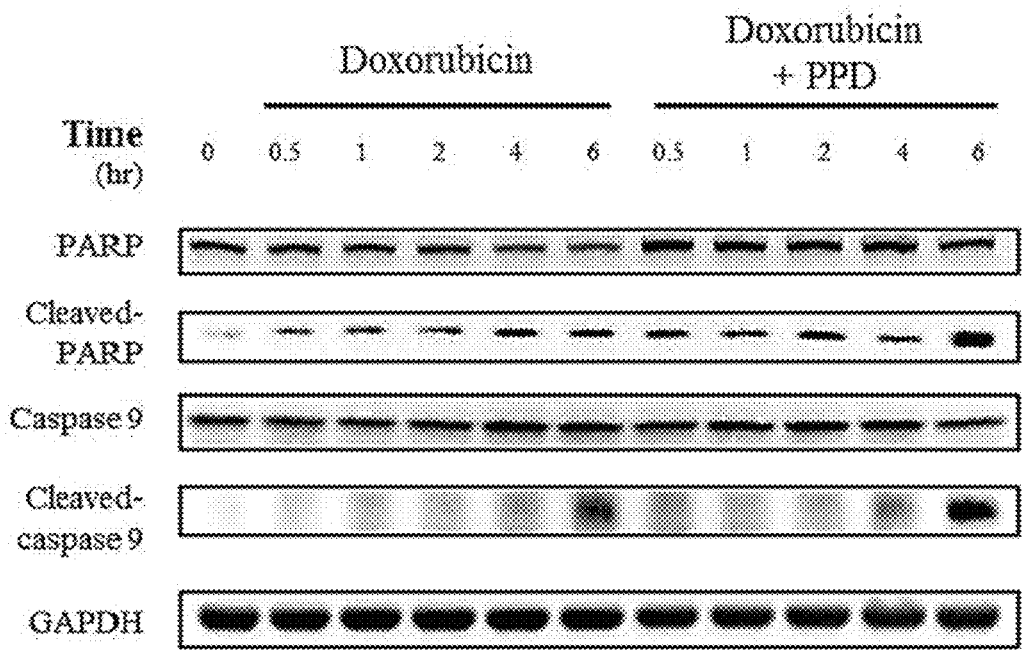
FIG. 3b is an image of Western blot analysis of comparison of expression levels of apoptosis-related proteins in a breast cancer cell simultaneously treated with doxorubicin and PPD depending on treatment time.

Accordingly, a culture medium containing 10 µg/mL of PPD was added to the MCF-7 cells, was cultured for 12 hours, and was then replaced with a culture medium containing 10 µg/mL of PPD and 5 µg/mL of doxorubicin, followed by 0, 0.5, 1, 2, 4, or 6 hours of culturing. Western blot analysis was performed using the cultured cells in the same manner as above (FIG. 3b). As a comparison group, cells cultured in a culture medium containing doxorubicin only was used instead of that containing both PPD and doxorubicin.

FIG. 3b is an image of Western blot analysis of comparison of expression levels of apoptosis-related proteins in a breast cancer cell simultaneously treated with doxorubicin and PPD depending on treatment time. As shown in FIG. 3b, it was confirmed that cleaved-PARP, and cleaved-caspase-9 were formed in the breast cancer cells simultaneously treated with PPD and doxorubicin faster than those treated only with doxorubicin.

Based on the results above, it could be understood that PARP and caspase-9 have an effect on the anticancer activity of doxorubicin. Accordingly, whether inhibition of the PARP and caspase-9 would inhibit the anticancer activity of doxorubicin was investigated.

Figure 3C:
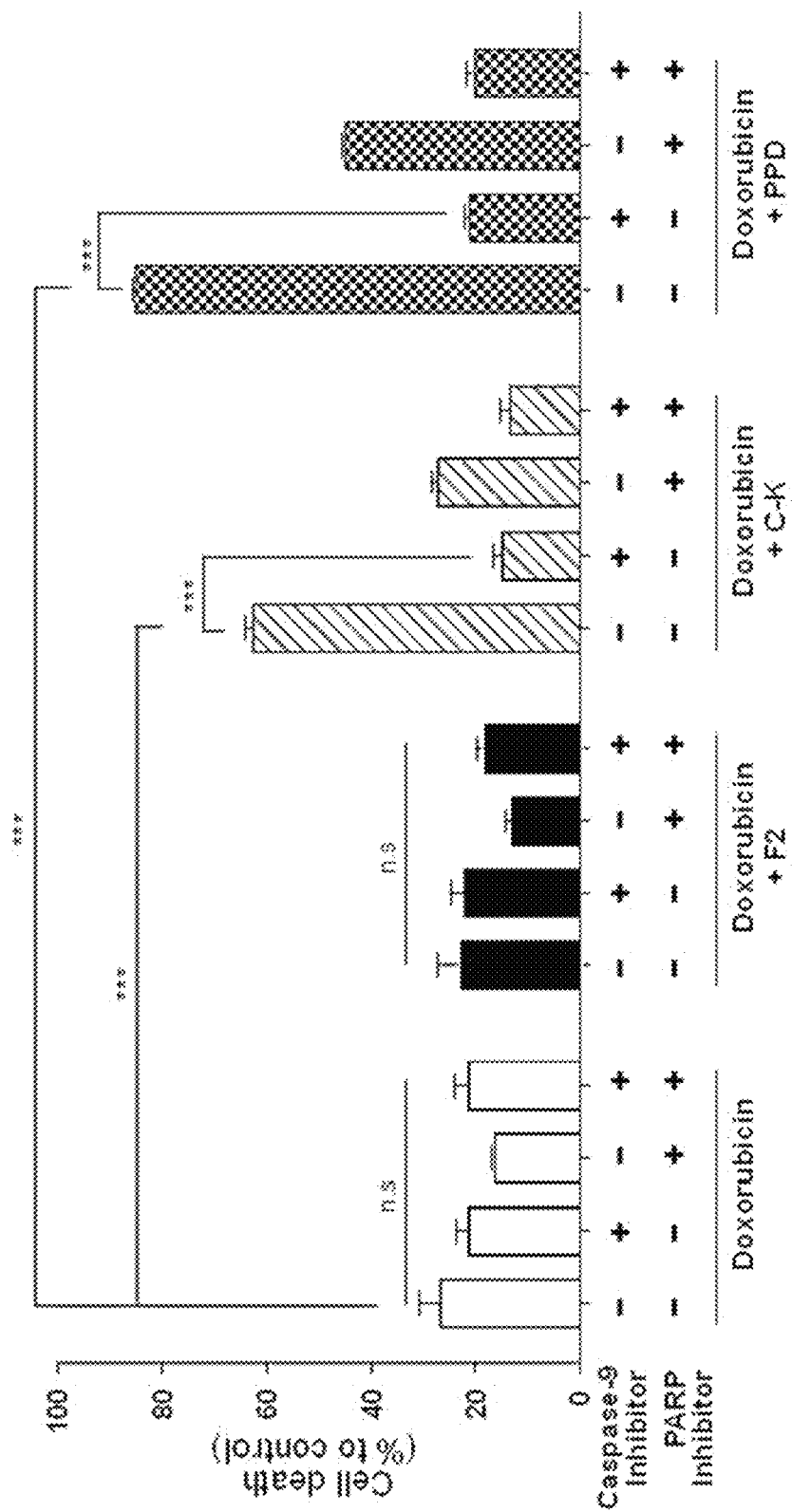
FIG. 3c is a graph showing a result of comparison of effects of PARP inhibitor or caspase-9 inhibitor with regard to the anticancer effect caused by the simultaneous treatment of doxorubicin and C-K or PPD.

Specifically, a culture medium containing 10 µg/mL of C-K or PPD was added to MCF-7 cells already treated with Z-LEHD-FMK, an inhibitor of caspase-9, or 3-AB, an inhibitor of PARP, was cultured for 12 hours, and was then replaced with a culture medium containing 10 µg/mL of C-K or PPD and 0 g/mL or 5 µg/mL of doxorubicin, followed by 24 hours of culturing. Western blot analysis was performed using the cultured cells in the same manner as above (FIG. 3c). An experiment group untreated with ginsenoside and F2, which is a PPD-type ginsenoside compound confirmed not to exhibit a particular effect on doxorubicin, were used as a negative control group and a positive control group, respectively.

FIG. 3c is a graph showing a result of comparison of effects of PARP inhibitor or caspase-9 inhibitor with regard to the anticancer effect caused by the simultaneous treatment of doxorubicin and C-K or PPD. As shown in FIG. 3c, it was confirmed that the anticancer effect of doxorubicin was inhibited in all control groups and experiment groups treated with a PARP or caspase-9 activity inhibitor. When treated with the PARP activity inhibitor, however, the anticancer activity of doxorubicin was somewhat recovered when the breast cancer cells were simultaneously treated with C-K or PPD and doxorubicin, which was investigated was due to the activity of caspase-9 existing in the upper region of the PARP.

Example 3: Effect of PDD on Mitochondria

From the result in Example 2, the PPD-type ginsenoside compound C-K or PPD was confirmed to promote the anticancer activity of doxorubicin, which is a type of the anticancer agent known to exhibit a mitochondria-mediated anticancer activity. In this regard, an effect of the C-K or PPD on mitochondria was investigated.

Example 3-1: Effect on Release of Cytochrome-C Induced in Mitochondria

Figure 4A:
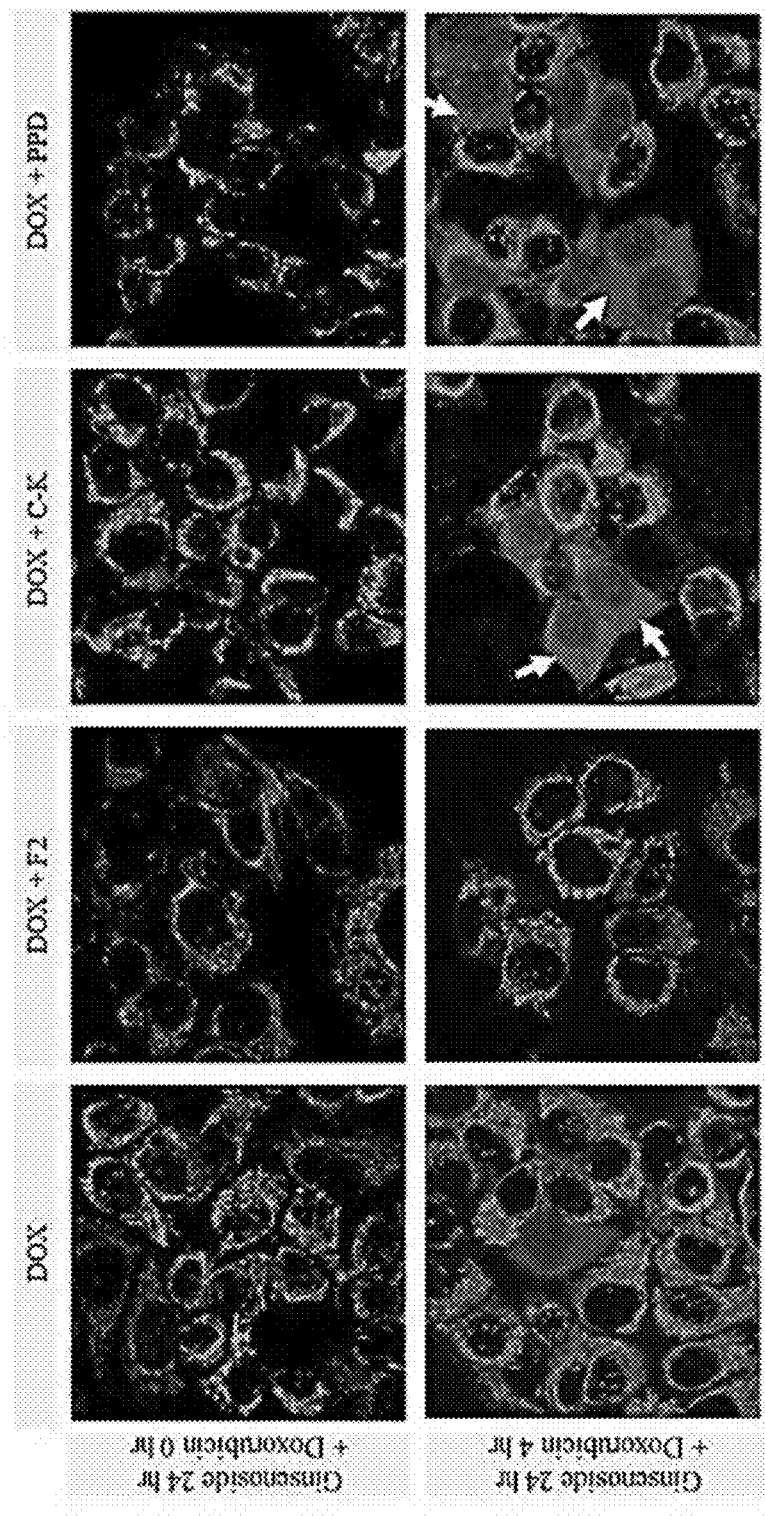
FIG. 4a is an image of immunofluorescent staining, showing a change in the level of cytochrome-C released from mitochondria simultaneously treated with doxorubicin and C-K or PPD.

A culture medium containing 10 µg/mL of C-K or PPD was added to MCF-7 cells, was cultured for 24 hours, and was then replaced with a culture medium containing 5 µg/mL of doxorubicin, followed by 0 or 4 hours of culturing. The cultured cells were fixed by adding 4% paraformaldehyde and were perforated by adding an 0.5% Triton X-100 solution, followed by 30 minutes of immunostaining using a cytochrome-C antibody. After staining, the cells were washed with PBS. Stained second antibodies were heated for 30 minutes and washed with PBS, followed by being recorded with a confocal microscope, to measure a level of fluorescence (FIG. 4a). An experiment group untreated with ginsenoside and F2, which is a PPD-type ginsenoside compound confirmed not to exhibit a particular effect on doxorubicin, were used as a negative control group and a positive control group, respectively.

FIG. 4a is an image of immunofluorescent staining, showing a change in the level of cytochrome-C released from mitochondria simultaneously treated with doxorubicin and C-K or PPD. As shown in FIG. 4a, in a case where doxorubicin was treated, the level of cytochrome-C release increased compared to a case where doxorubicin was not treated. It was confirmed that an increase in the level of cytochrome-C release was higher when treated with both doxorubicin and C-K or PPD compared to when treated with doxorubicin alone.

Figure 4B:
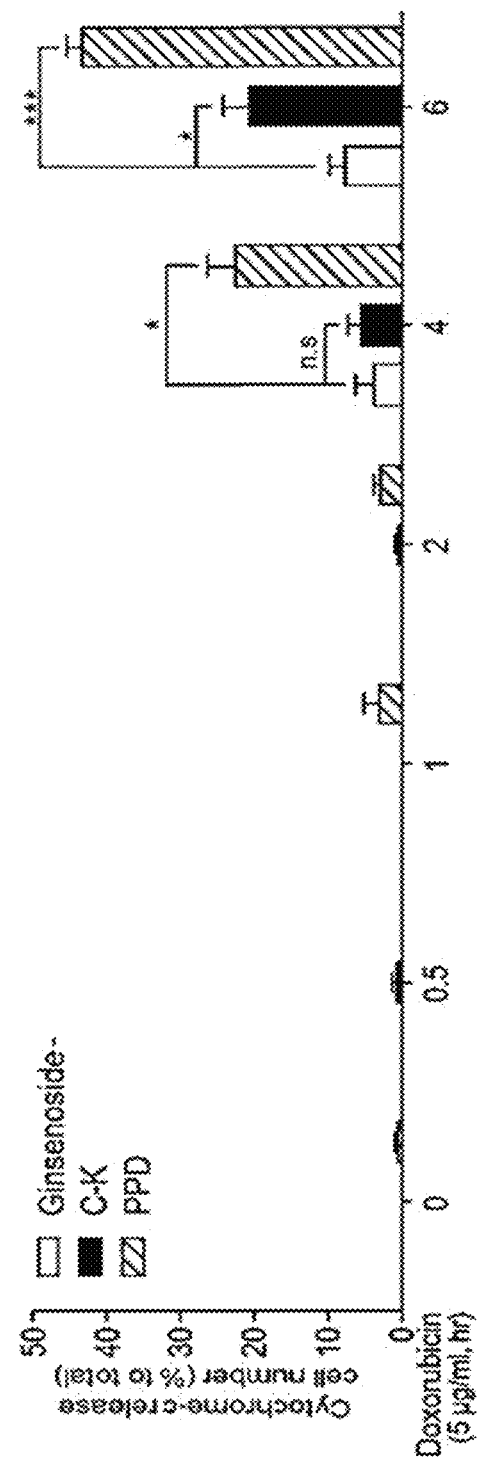
FIG. 4b is a graph showing the number of cells in which cytochrome-C is released from mitochondria according to the treatment time of doxorubicin and C-K or PPD.

In this regard, whether the level of cytochrome-C release changes depending on treatment time of doxorubicin was investigated. In other words, a culture medium containing 10 µg/mL of C-K or PPD was added to MCF-7 cells, was cultured for 24 hours, and was then replaced with a culture medium containing 5 µg/mL of doxorubicin, followed by 0, 0.5, 1, 2, 4, or 6 hours of culturing. The immunofluorescent staining was performed in the same manner as previously described except the culturing time to measure the number of cytochrome-C released into cytoplasm from mitochondria (FIG. 4b). As a control group, an experiment group untreated with ginsenoside was used.

FIG. 4b is a graph showing the number of cells in which cytochrome-C is released from mitochondria according to the treatment time of doxorubicin and C-K or PPD. As shown in FIG. 4b, cytochrome-C was released from 7% of the total cells in the control group treated only with doxorubicin after 6 hours, whereas cytochrome-C was released from 20% and 43% of the total cells in the experiment group treated with C-K and doxorubicin and that treated with PPD and doxorubicin, respectively.

Accordingly, it could be understood that C-K or PPD exhibits a function of promoting cytochrome-C release mediated by doxorubicin in mitochondria.

Example 3-2: Effect on Inducing Mitochondrial Damage

From the result in Example 3-1, it was confirmed that C-K or PPD can promote cytochrome-C release mediated by doxorubicin in mitochondria. In this regard, whether C-K or PPD can damage mitochondria was investigated.

In other words, a culture medium containing 10 μg/mL of C-K or PPD was added to MCF-7 cells and was cultured for 24 hours. The cultured cells were fixed by adding 4% paraformaldehyde and were perforated by adding a 0.5% Triton X-100 solution, followed by staining the mitochondria using Tom-20. The stained cells were washed with PBS and were recorded with a confocal microscope to measure a level of fluorescence (FIG. 5a). An experiment group untreated with ginsenoside and F2, which is a PPD-type ginsenoside compound confirmed not to exhibit a particular effect on doxorubicin, were used as a negative control group and a positive control group, respectively.

FIG. 5a is an image showing a result of fluorescence staining of mitochondria included in a MCF-7 cell treated with C-K or PPD. As shown in FIG. 5a, compared to the mitochondria of the negative control group, those of the positive control group did not show particular changes. However, the mitochondria included in the MCF-7 cells treated with C-K or PPD were damaged.

In this regard, Western blot analysis was performed for each cultured cell to compare an expression level of the mitochondrial fission-related proteins (Drp1, Fis1, or OPA-3) and mitochondrial fusion-related proteins (Mfn1. Mfn2, or OPA1) (FIG. 5b).

FIG. 5b is an image of Western blot analysis showing expression levels of mitochondrial fission-related proteins (Drp1, Fis1, and OPA-3) and mitochondrial fusion-related proteins (Mfn1, Mfn2, and OPA1), which are expressed in a MCF-7 cell treated with C-K or PPD. As shown in FIG. 5b, in the MCF-7 cells treated with C-K or PPD, the expression level of the mitochondrial fission-related protein OPA-3 increased, whereas that of mitochondrial fusion-related protein Mfn2 decreased.

In summary of the results of Examples 3-1 and 3-2 above, as C-K or PPD may induce mitochondrial damage, C-K or PPD increases cytochrome-C release from mitochondria by treatment with doxorubicin, thereby enhancing the anticancer activity of doxorubicin in case of treating with both C-K or PPD and doxorubicin.

Example 4: Analysis of Correlation Between Mitochondrial Fission and Anticancer Activity of Doxorubicin From the result of Example 3-2 above, as it was confirmed that C-K or PPD induces mitochondrial damage, mitochondrial fission was induced by inhibiting mitochondrial fusion-related protein expression (Mfn1 or Mfn2), followed by treating with doxorubicin to analyze a correlation between mitochondrial fission and the anticancer activity of doxorubicin.

Specifically, a siRNA targeting Mfn1 and Mfn2 was synthesized, while synthesizing a random siRNA as a negative control group.

```
                                         (SEQ ID NO: 1)
Control group:  5'-CCUACGCCAAUUUCGU-3'-dTdT (SEQ ID NO: 2)
Mfn1:           5'-GUGUAGAUUCUGGUAAUGA-3'-dTdT (SEQ ID NO: 3)
Mfn2:           5'-CGAUGCAACUCUAUCGUCA-3'-dTdT
```

Each synthesized siRNA was inoculated into an MCF-7 cell and was cultured for 12 hours. The cells were again cultured in a standard culture medium in which siRNA is not contained for 48 hours to measure an expression level of mitochondrial fusion-related protein (Mfn1 or Mfn2) expressed therein via Western blot analysis (FIG. 6a).

Figure 6A:
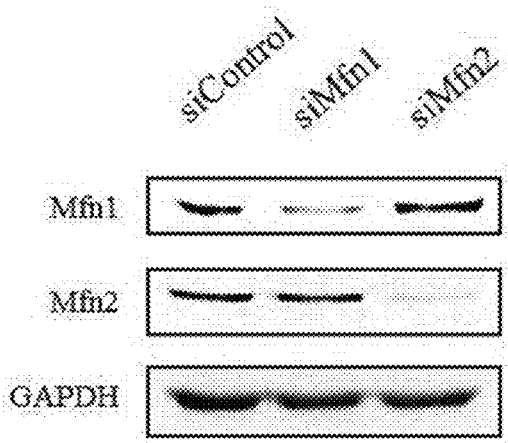
FIG. 6a is an image of Western blot analysis showing a result which confirms inhibition of mitochondrial fusion-related protein (Mfn1 and Mfn2) expression by siRNA which inhibits the expression of said proteins.

FIG. 6a is an image of Western blot analysis showing a result which confirms inhibition of mitochondrial fusion-related protein (Mfn1 and Mfn2) expression by siRNA which inhibits the expression of said proteins. As shown in FIG. 6a, it was confirmed that the expression of the mitochondrial fusion-related proteins (Mfn1 or Mfn2) was inhibited by the siRNA inoculation.

Figure 6B:
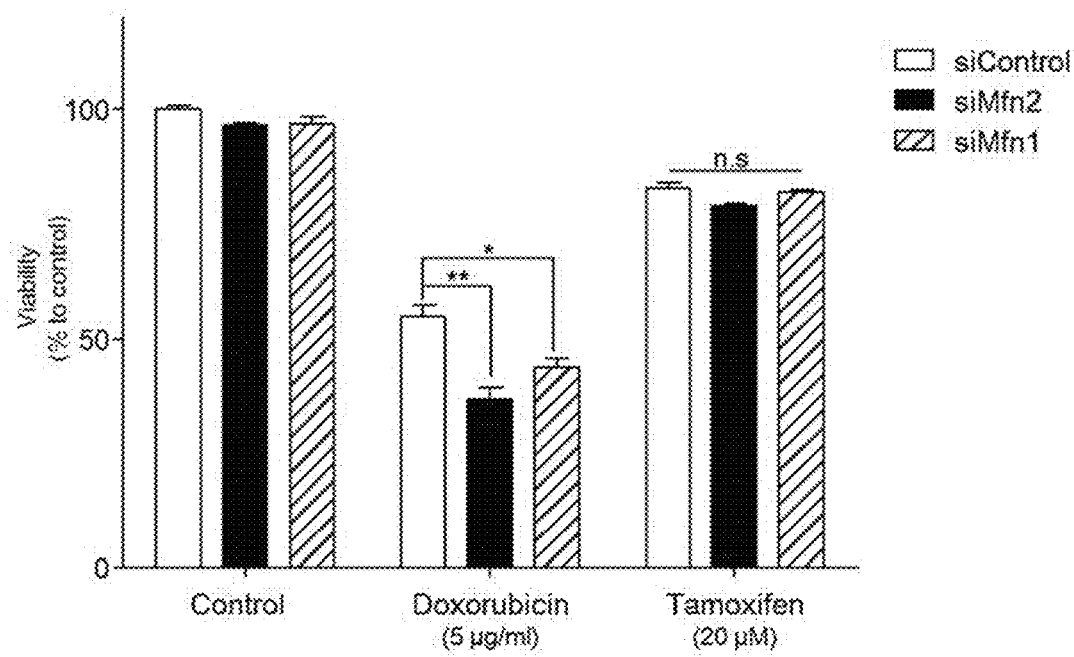
FIG. 6b is a graph showing a result of comparison of anticancer activities of doxorubicin and tamoxifen on a cell with mitochondrial fission.

Meanwhile, each synthesized siRNA was inoculated into MCF-7 cells and was cultured for 12 hours. The cells were again cultured in a standard culture medium in which siRNA is not contained for 48 hours, followed by treating with 5 μM doxorubicin or 20 μM tamoxifen and culturing for 24 hours. After culturing, viabilities of the MCF-7 cells were measured via WST-1 analysis (FIG. 6b). As a control group, cells cultured without treating with doxorubicin or tamoxifen were used.

FIG. 6b is a graph showing a result of comparison of anticancer activities of doxorubicin and tamoxifen on a cell with mitochondrial fission. As shown in FIG. 6b, the viability of the cells which were not treated with doxorubicin or tamoxifen did not decrease even after mitochondrial fission was induced, whereas when treated with doxorubicin or tamoxifen, the cells showed the anticancer activity. In particular, the cell treated with doxorubicin, compared to that with tamoxifen, showed significantly higher anticancer activity. Additionally, it was confirmed that when mitochondrial fission is induced, the anticancer activity of doxorubicin significantly increased when Mfn2 expression was inhibited compared to when Mfn1 expression was inhibited. However, when tamoxifen was treated, there was no difference in the anticancer activity depending on the treatment of each siRNA.

Figure 7:
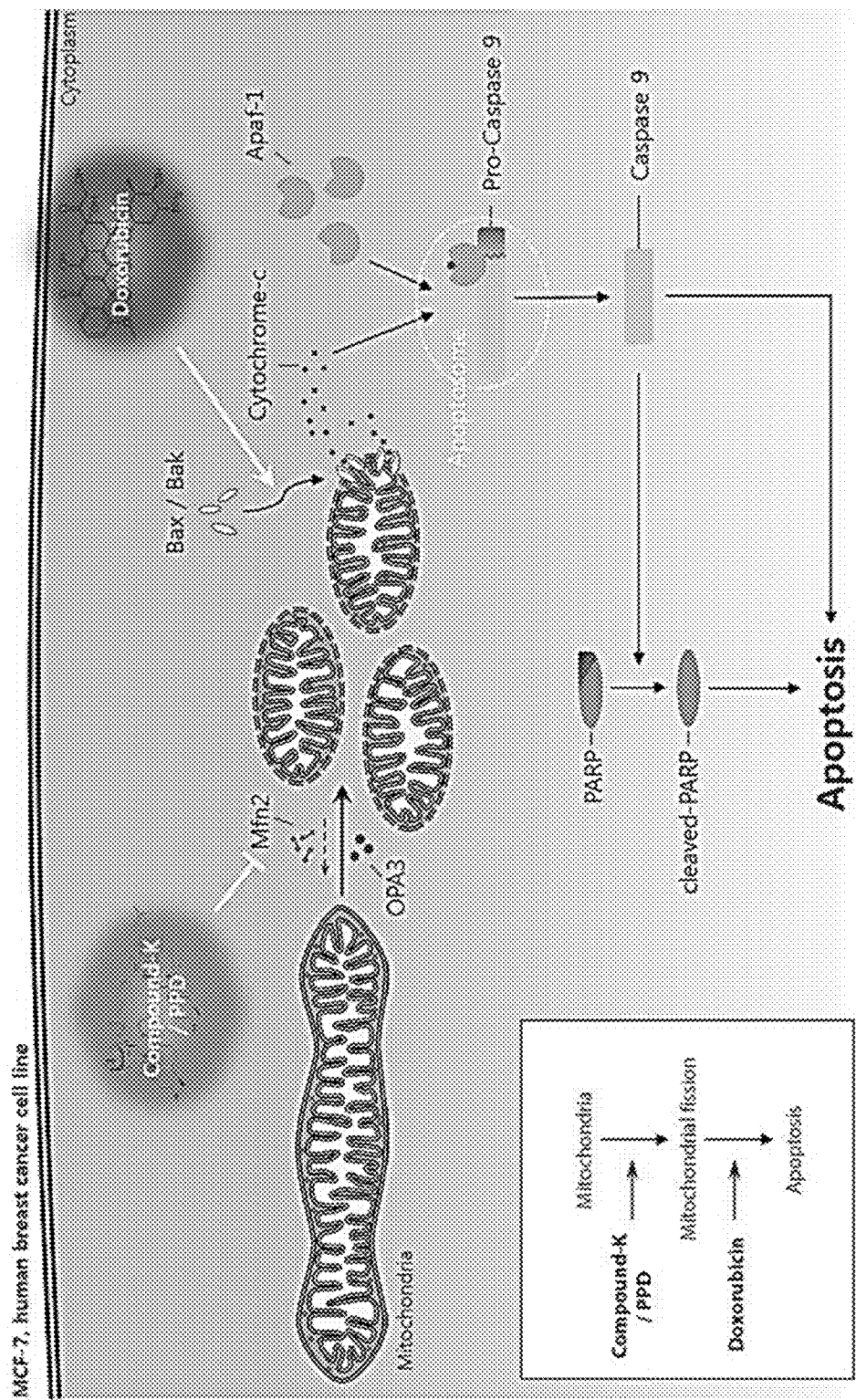
FIG. 7 is a schematic diagram of the mechanism of the anticancer supplement agent and the anticancer agent which exhibits a mitochondria-mediated anticancer activity provided in the present invention.

In summary of the results of Examples 1 to 4, as shown in FIG. 7, PPD or C-K, which belongs to the PPD-type ginsenoside compound, promotes mitochondrial fission by inhibiting the mitochondrial fusion-related protein Mfn2 expression, thereby causing mitochondrial damage. When the cancer cell is treated with an anticancer agent (i.e., doxorubicin) that shows mitochondria-mediated anticancer activity under such condition, more damage results in the damaged outer membrane of mitochondria, and more cytochrome-C is released from the mitochondria to the cytoplasm. The released cytochrome-C induces apoptosis through apoptosome, resulting in death of the cancer cells.

Therefore, it could be understood that when C-K or PPD and an anticancer agent exhibiting a mitochondria-mediated anticancer activity are used in combination, safer anticancer therapy can be performed by reducing administration amount of the anticancer agent.

The invention claimed is:

1. A method for screening a regulator of mitochondrial fission, comprising:
   (a) treating an isolated cell with protopanaxadiol (PPD) of Formula 1 or compound-K (C-K) of Formula 2 and a candidate compound expected to be capable of regulating mitochondrial fission;
   (b) measuring a level of mitochondrial fission within the cell treated with the candidate compound; and
   (c) selecting a candidate compound promoting or inhibiting the mitochondrial fission in comparison with a negative control which is not treated with the candidate compound, wherein Formula 1 and Formula 2 comprise:

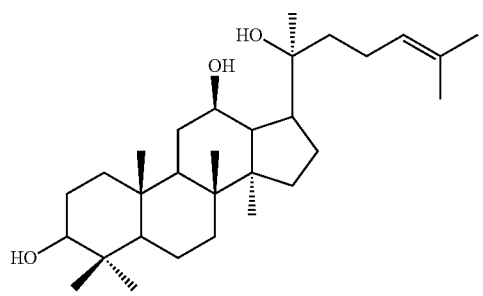

Formula 1

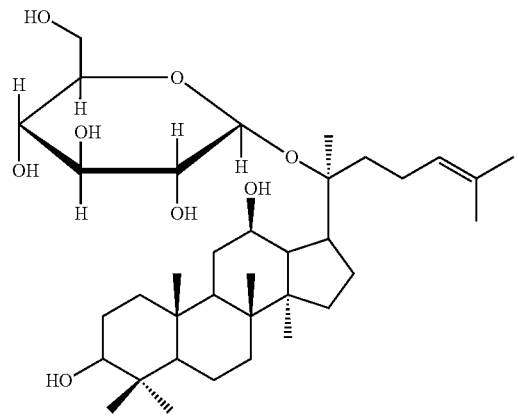

Formula 2

2. The method of claim 1, wherein the isolated cell is an insulinotropic cell or a tumor cell.

* * * * *

SEQUENCE LISTING

```
<160> NUMBER OF SEQ ID NOS: 3

<210> SEQ ID NO 1
<211> LENGTH: 16
<212> TYPE: RNA
<213> ORGANISM: Artificial Sequence
<220> FEATURE:
<223> OTHER INFORMATION: siRNA

<400> SEQUENCE: 1
ccuacgccaa uuucgu                                              16

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
guguagauuc ugguaauga                                           19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
cgaugcaacu cuaucguca                                           19
```